United States Patent
Miller et al.

(10) Patent No.: US 7,141,378 B2
(45) Date of Patent: Nov. 28, 2006

(54) EXPLORING FLUOROPHORE MICROENVIRONMENTS

(75) Inventors: Steven C. Miller, Union City, CA (US); Paul B. Comita, Menlo Park, CA (US); Evan F. Cromwell, Redwood City, CA (US); Christopher B. Shumate, Carlsbad, CA (US)

(73) Assignee: Blueshift Biotechnologies, Inc., Sunnyvale, CA (US)

( * ) Notice: Subject to any disclaimer, the term of this patent is extended or adjusted under 35 U.S.C. 154(b) by 0 days.

(21) Appl. No.: 11/173,814

(22) Filed: Jul. 1, 2005

(65) Prior Publication Data

US 2006/0003320 A1    Jan. 5, 2006

Related U.S. Application Data

(60) Provisional application No. 60/585,229, filed on Jul. 2, 2004.

(51) Int. Cl.
*C12Q 1/68* (2006.01)
*G01N 33/53* (2006.01)

(52) U.S. Cl. .......................................... 435/6; 435/7.1
(58) Field of Classification Search .................. 435/6, 435/7.1
See application file for complete search history.

(56) References Cited

U.S. PATENT DOCUMENTS

| | | | |
|---|---|---|---|
| 4,855,930 A | 8/1989 | Chao | |
| 4,893,008 A | 1/1990 | Horikawa | |
| 5,310,674 A | 5/1994 | Weinreb et al. | |
| 5,338,753 A | 8/1994 | Burnstein et al. | |
| 5,355,215 A | 10/1994 | Schroeder et al. | |
| 5,485,530 A | 1/1996 | Lakowicz et al. | |
| 5,506,141 A | 4/1996 | Weinreb et al. | |
| 5,585,639 A | 12/1996 | Dorsel et al. | |
| 5,597,696 A * | 1/1997 | Linn et al. | 435/6 |
| 5,631,169 A | 5/1997 | Lakowicz et al. | |
| 5,718,915 A | 2/1998 | Virtanen et al. | |
| 5,807,522 A * | 9/1998 | Brown et al. | 422/50 |
| 5,997,861 A | 12/1999 | Virtanen et al. | |
| 6,030,581 A | 2/2000 | Virtanen | |
| 6,097,485 A | 8/2000 | Lievan | |
| 6,187,267 B1 | 2/2001 | Taylor et al. | |
| 6,196,979 B1 | 3/2001 | Virtanen | |
| 6,197,534 B1 | 3/2001 | Lakowicz et al. | |
| 6,274,373 B1 | 8/2001 | Virtanen | |
| 6,310,687 B1 | 10/2001 | Stumbo et al. | |
| 6,312,901 B1 | 11/2001 | Virtanen | |
| 6,322,682 B1 | 11/2001 | Arvidsson et al. | |
| 6,327,031 B1 | 12/2001 | Gordon | |
| 6,331,275 B1 | 12/2001 | Virtanen | |
| 6,342,349 B1 | 1/2002 | Virtanen | |
| 6,379,699 B1 | 4/2002 | Virtanen et al. | |
| 6,384,951 B1 | 5/2002 | Basiji et al. | |
| 6,395,556 B1 | 5/2002 | Lakowicz et al. | |
| 6,403,367 B1 | 6/2002 | Hoyt et al. | |
| 6,406,293 B1 | 6/2002 | Burstein | |
| 6,454,970 B1 | 9/2002 | Ohman | |
| 6,459,484 B1 | 10/2002 | Yokoi | |
| 6,462,809 B1 | 10/2002 | Ryan et al. | |
| 6,503,359 B1 | 1/2003 | Virtanen | |
| 6,509,161 B1 | 1/2003 | Barker et al. | |
| 6,566,069 B1 | 5/2003 | Virtanen | |
| 6,620,478 B1 | 9/2003 | Öhman | |
| 6,632,656 B1 | 10/2003 | Andersson et al. | |
| 6,653,625 B1 | 11/2003 | Andersson et al. | |
| 6,717,136 B1 | 4/2004 | Andersson et al. | |
| 6,728,644 B1 | 4/2004 | Bielik et al. | |
| 6,811,736 B1 | 11/2004 | Ohman et al. | |
| 6,812,456 B1 | 11/2004 | Andersson et al. | |
| 6,812,457 B1 | 11/2004 | Andersson et al. | |
| 2001/0052976 A1 | 12/2001 | Juncosa et al. | |
| 2002/0055179 A1 | 5/2002 | Busey et al. | |
| 2003/0030850 A1 | 2/2003 | Heffelfinger et al. | |
| 2004/0071332 A1 | 4/2004 | Bruce et al. | |

FOREIGN PATENT DOCUMENTS

| | | |
|---|---|---|
| EP | 0 440-342 A | 8/1991 |
| WO | 00/043780 | 7/2000 |
| WO | WO 00/71991 A | 11/2000 |
| WO | WO 02/35474 A | 5/2002 |
| WO | WO 2004/017374 A2 | 2/2004 |

OTHER PUBLICATIONS

International Search Report dated May 4, 2006 from related International Application No. PCT/US05/23520.

(Continued)

*Primary Examiner*—Ethan Whisenant
(74) *Attorney, Agent, or Firm*—Beyer Weaver & Thomas, LLP

(57) ABSTRACT

Methods, apparatus, and system, implementing and using techniques for detecting a presence of one or more target analytes in particular regions of interest of one or more samples. One or more samples including objects and one or more target analytes are provided. Some of the target analytes are labeled with a fluorophore and are bound to some of the objects in the samples. The samples are illuminated with fluorescence inducing light and fluorescent light is collected from one or more regions of the one or more samples. At least one anisotropy measurement of the samples is performed to identify regions of interest where one or more target analytes are bound to the objects. The collected fluorescent light from the regions of interest is analyzed to determine a presence of target analytes that are bound to the objects in the one or more samples.

19 Claims, 4 Drawing Sheets

OTHER PUBLICATIONS

Mere et al., "Miniaturized FRET assays and microfluidics: key components for ultra-high-throughput screening," Aug. 1999, vol. 4 4, No. 8, DDT.

Gonzalez et al., Cellular Fluorescent Indicators and Voltage/Ion Probe Reader (VIPR™): Tools for Ion Channel and Receptor Drug Discovery, Taylor & Francis healthsciences, Receptors and Channels, 8:283-295, 2002.

Lakowicz et al., "Anisotropy-Based Sensing with Reference Fluorophores," Oct. 20, 1998, Analytical Biochemistry 267, 397-405 (1999).

Heather Thompson, "Compact Discs May Play a Role in Diagnosis," Jul. 2004, MDDI.

Chad Boutin, "BioCDs could hit No. 1 on doctos' charts," May 18, 2004, Purdue News.

"Products: Optical LiveCell™ Array," Molecular Cytomics, http://www.molecular-cytomics.com/LiveCell.htm, downloaded Apr. 28, 2005.

Manoj M. Varma[a] et al., "High-Speed Label-Free Multi-Analyte Detection through Micro-interferometry," Proceedings of SPIE vol. 4966, SPIE, 2003.

* cited by examiner

EXPLORING FLUOROPHORE MICROENVIRONMENTS

CROSS REFERENCE TO RELATED APPLICATIONS

The present application claims priority to Provisional Application No. 60/585,229, entitled "Exploring Fluorophore Microenvironments by Anisotropy and Kinetics," filed Jul. 2, 2004, which is incorporated herein by reference. The present application is also related to patent application Ser. No. 10/927,748, entitled "Time dependent fluorescence measurements," filed Aug. 26, 2004, and to patent application Ser. No. 10/928,484, entitled "Measuring time dependent fluorescence," filed Aug. 26, 2004, both of which are incorporated herein by reference.

BACKGROUND

This invention relates to measuring fluorescence and properties derived from fluorescence in materials Fluorescence refers to the property of some atoms and molecules to absorb light at a particular wavelength and to subsequently emit light of longer wavelength after a brief time interval, termed the fluorescence lifetime. Fluorescence illumination and observation is a rapidly expanding technique employed today, both in the medical and biological sciences. This has spurred the development of various kinds of sophisticated microscopes and other equipment that is suitable for analyzing fluorescence signals.

Fluorescent probes used in biological applications are typically constructed around synthetic aromatic organic chemicals designed to bind with a biological macromolecule. Fluorescent dyes are also useful in monitoring cellular integrity (e.g., live versus dead and apoptosis), endocytosis, exocytosis, membrane fluidity, protein trafficking, signal transduction, enzymatic activity, and so on. In addition, fluorescent probes have been widely applied to genetic mapping and chromosome analysis in the field of molecular genetics.

Some properties of fluorescent signals that have been used in biological applications include fluorescence intensity, fluorescence polarization/anisotropy, and fluorescence lifetime. Fluorescence intensity can be used to provide an indication of the presence (and possibly also the amount) of a particular fluorophore in a sample. Fluorescence anisotropy can provide a measure of the degree to which fluorescent radiation is non-randomly polarized, that is, the degree to which one polarization orientation predominates over its orthogonal polarization orientation. A highly anisotropic signal is highly polarized (for example, linearly polarized). A highly isotropic signal approaches random polarization. In one conventional approach, anisotropy (r) is calculated using the following equation:

$$r = \frac{VV - gVH}{VV + 2gVH}$$

where VH and VV are the horizontal and vertical polarizations (relative to vertically polarized excitation light) and g corrects for polarization bias of the optical instrument used to detect the fluorescence. Fluorescence lifetime can be used, for example, to classify the microenvironment of a particular analyte in a sample.

Many of today's fluorescence analysis systems work well in laboratory settings. However, in the chemical and biotechnology industry, there is often a need to analyze a large number of samples in a time and cost-efficient manner. Due to the different requirements in these environments, many fluorescence analysis systems are not suitable or possible to use and, as a result, the range of analyses that can be performed in an industrial setting is more limited than that of a laboratory setting.

SUMMARY

In general, in one aspect, the invention provides methods, apparatus, and system, implementing and using techniques for detecting a presence of one or more target analytes in particular regions of interest of one or more samples. One or more samples including a plurality of objects and one or more target analytes are provided. At least some of the target analytes are labeled with a fluorophore and are bound to at least some of the objects in the one or more samples. The one or more samples are illuminated with fluorescence inducing light, and fluorescent light is collected from one or more regions of the one or more samples. At least one anisotropy measurement of the one or more samples is performed to identify one or more regions of interest where one or more target analytes are bound to the objects. The collected fluorescent light from the regions of interest is analyzed to determine a presence of target analytes that are bound to the objects in the one or more samples.

Advantageous implementations can include one or more of the following features. The regions of interest can be identified as regions of the sample having a measured anisotropy value that exceeds a predetermined threshold value, and fluorescent light can be collected from only confined detection regions within the identified regions of interest. Analyzing the fluorescent light can include analyzing fluorescent light collected from the identified regions of interest only. The objects can be spots, microbeads, cells, and microarrays. At least some objects can be optically encoded by one or more of: fluorophores, quantum dots or other materials with a distinct response to excitation light.

Providing a sample can include providing optically encoded objects that each has an affinity to an analyte and an optical signature corresponding to the analyte; contacting the objects with a sample containing one or more analytes having a first affinity moiety to at least one target analyte and a second affinity moiety to at least some of the optically encoded objects, whereby the first affinity moiety of at least some analytes in the sample bind to the optically encoded objects; and contacting the optically encoded objects and their bound analytes with a target sample containing one or more target analytes under conditions allowing the target analytes to bind to the second affinity moiety of the analytes in the sample.

The analyzing can include detecting a binding reaction occurring at one or more of the objects, classifying target analytes at one or more of the objects, and enumerating the one or more objects. The provision of the one or more samples can be performed under homogenous conditions that do not involve any wash steps. The second affinity moiety can be an antibody, an antigen, a receptor, a ligand, a nucleic acid, an enzyme, a substrate inhibitor, and an analogous moiety. The target analytes can be an antibody, an antigen, a receptor, a ligand, a protein, a peptide, an enzyme, a nucleic acid, a drug, a hormone, a chemical, a pathogen, a toxin, a bacterium, or a virus. The collecting and analyzing can be performed for up to about 20,000 objects per second.

Each optically encoded object can be individually classifiable based on its emitted fluorescent light.

Collecting can include collecting fluorescence intensity values, fluorescence polarization values, fluorescence anisotropy values, rotational correlation times, and fluorescence lifetimes. The illuminating, collecting and analyzing can be performed in multiple fluorescence wavelength regions. Analyzing can include measuring changes with respect to time of the collected fluorescent light to provide kinetic information. Concentrations for the target analytes can be determined based on measured changes in intensity values of the collected fluorescent light over time or based on measured changes in anisotropy values of the collected fluorescent light over time. Individual objects that contain bound target analytes can be determined based on measured changes in anisotropy values of the collected fluorescent light over time. Objects that each has a known anisotropy can be provided, whereby an internal anisotropy reference is formed, and the measured anisotropy can be compared to the anisotropy of the objects with known anisotropy in order to obtain an improved anisotropy measurement of the bound target analyte.

The details of one or more embodiments of the invention are set forth in the accompanying drawings and the description below. Other features and advantages of the invention will be apparent from the description and drawings, and from the claims.

DESCRIPTION OF DRAWINGS

Like reference symbols in the various drawings indicate like elements.

DETAILED DESCRIPTION

Figure 1:
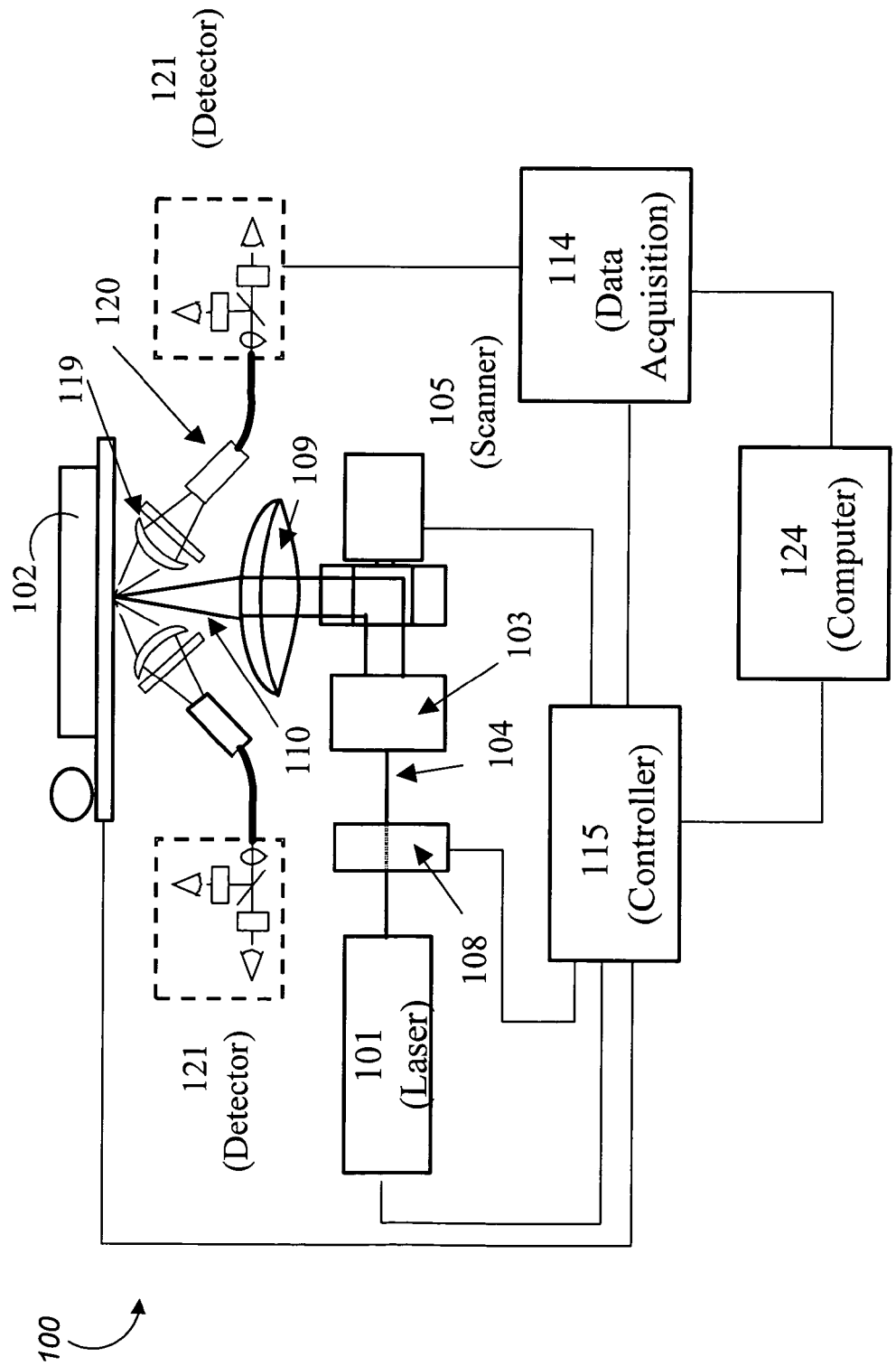
FIG. 1 is a schematic view of an apparatus for collecting optical data in accordance with a first embodiment of the present invention.

A specific embodiment of the invention is described in detail below. An example of this embodiment is also illustrated in the accompanying drawings. While the invention will be described in conjunction with this specific embodiment, it will be understood that the description is not intended to limit the invention to a single embodiment. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general, in one aspect, the invention provides methods and apparatus, implementing and using techniques for exploring fluorophore microenvironments by anisotropy and kinetics, and in particular for measuring binding reactions using anisotropy and kinetics. Anisotropy measurements performed in accordance with various embodiments of the apparatus and methods of the invention allow free fluorophore in a sample solution to be distinguished from immobilized fluorophore in the sample. As will also be described below, the system and methods of the invention provide a robust real-time technology for spot, bead, and cell classification and enumeration. Kinetic measurements provide an improved method for quantitation that is independent of the total fluorescence signal recorded. The anisotropy measurements of the sample also make it possible to use the measured anisotropy values as a gating function and, for example, collect fluorescent light only from regions of interest of the sample having an anisotropy value that exceeds a particular threshold value. Alternatively, fluorescent light can be collected from the entire sample, but only be analyzed for regions of interest of the sample having an anisotropy value that exceeds the threshold value.

In certain embodiments, the laser scanning system used to perform measurements in accordance with the invention is designed for highly miniaturized end-point and kinetic binding assays using microarray spots, beads, or cells. The system can monitor homogeneous binding reactions in real-time and in simple microscale formats. The technology and data processing methods of the system enable homogeneous assays, that is, in-situ assays that do not require any or minimal wash steps, which is typically the case for conventional assays. The assays can be used to identify, characterize, and analyze multistep and multi-molecular events, such as many different formats of in vitro assays involving various binding moieties such as antibodies, biotin or streptavidin, and so on. Many "sandwich" structures can be produced in the assays depending on the type of target analyte, the substrate, etc. As a specific example, an antibody array may be employed in a 96 well plate. The target analyte may be pre-labeled with a detection moiety (e.g., a fluorophore) prior to contact with the substrate (and binding) or afterwards. In either case, the resulting multi-level structure can be scanned with the above-described system, using, e.g., a green 532 nm laser excitation wavelength. The detection occurs in real time within seconds and the bound fluorophores exhibit a distinctly higher anisotropy than the fluorophores that are still free in the sample solution.

It should be noted that the size of the biotinylated fluorophores are relatively small, so that their mobility is sufficient during the fluorescent lifetime to distinguish free fluorophores from bound fluorophores using anisotropy measurements. If the biotinylated fluorophores were large, they would move slowly, which would make it difficult to distinguish free fluorophores from bound fluorophores during the fluorescence lifetime, and thus make it impractical to detect binding through the use of anisotropy. It should however be noted that if fluorophores with longer lifetime are used, larger molecules can be studied, since they could be studied during a sufficient time period, that is, before the fluorescence lifetime has passed, to detect whether they are bound or free.

In general, techniques described herein can also be used to detect protein-protein interactions, for example, by having a "capture protein" bound to a substrate and introducing "target proteins" in a solution and allowing them to bind to the capture proteins. Depending on the type of experiments being performed, the fluorophore can either be introduced after the target analyte has been introduced, or the target analyte can be pre-labeled with the fluorophore before introduction.

An example system that can be used for performing the analyses of the present invention is further described in the co-pending U.S. patent application Ser. No. 10/927,748, and U.S. patent application Ser. No. 10/928,484, both of which are incorporated by reference above. A brief overview of the laser scanning system will now be presented. In the described embodiment, the system uses a scanning light source, which can be focused onto a substrate containing samples, with the ability to discriminate against background noise or signal, and makes use of image contrast mechanisms. The system can be operated in several distinct modes or combinations thereof, depending on what type of sample data needs to be collected.

In a first mode, the output signal from the system contains information such as the number of discrete positions in a biological cell (which, for example, enables the study of localization of various molecules in the cell) or other object from which the fluorescent light originates, the relative location of the signal sources, and the color (e.g., wavelength or waveband) of the light emitted at various positions of the samples. In a second mode, a plane-polarized laser beam can be propagated through the optical system onto the samples, allowing interrogation of biological material with polarized light. The polarized nature of the excitation source allows for measurement of properties of biological materials where the characteristics of the anisotropy of the emission, or the time dependent nature of the relaxation of the polarization, can give rise to spatial or physical information about the biological moiety.

In a third mode, several laser beams can be propagated through the optical system onto the samples allowing interrogation of the biological material with different wavelengths of light or with the same wavelength at different times. In this mode the lasers can be pulsed simultaneously or with a fixed or variable delay between pulses. Delay between pulses allows for measurement of properties of biological materials in an excited state where the first laser pulse causes excitation of the biological moiety and the second or additional laser pulses interrogate that moiety in an excited state. The laser beams can be co-propagated so that they focus on the same sample during a scan or, alternatively, they can be propagated at some relative angle so that during a scan the laser beams sequentially move over the same sample.

In a fourth mode, a single modulated laser beam can be propagated through the optical system onto the sample allowing lifetime measurements of the fluorescence in the biological material. In a fifth mode, several detectors can be used in conjunction with one collection optics arrangement, which creates multiple confinement regions for analysis, the advantages of which will be described in further detail below. The confinement regions are typically vertical regions with a thickness of, for example, about 100–200 microns, located at the bottom of a sample well or substrate from which fluorescence is collected. The confinement regions are described in detail in the above referenced patent applications, and will be briefly described below. By collecting signal only at a precise depth within an assay milieu, signal quality can be greatly enhanced. The confinement region is preferably set be the depth where a fluorophore (or other signal producing moiety) binds to the substrate. In a sixth mode, several collection optics arrangements can be used to provide improved confinement over a single collection optic with the unique geometry, or can be used to collect emission from the confined region with several characteristics which are uniquely specified to each collecting optics, the advantages which will be described below.

As shown in FIG. 1, in one embodiment of the system an excitation light source (101) emits excitation light (104) to be projected onto a substrate (102) containing samples that are to be investigated. The substrate (102) will be described in further detail below. Typically, the excitation light source (101) is a laser, such as an Ar or Ar/Kr mixed gas laser with excitation lines of 488, 514, 568 and 647 nm. In one embodiment, a continuous wave (CW) laser, such as the Compass 315 M laser from Spectraphysics Inc. of Mountain View, Calif., is used as an excitation source. Depending on the laser (101) and specific optics used in the system, the wavelength of the excitation light can be either within the visible range (i.e., 400–700 nm), or outside the visible range. For excitation wavelengths below 400 nm photochemical reaction rates, such as those due to photobleaching, tend to be substantial. In one embodiment, the output from the laser (101) can be modulated and provide information about the time dependent response of fluorescence signals by using a frequency modulation detection scheme. In another embodiment, a pulsed laser with laser pulses of approximately 12 ps FWHM (Full Width at Half Max) with a spacing of approximately 12 ns is used as the excitation light source (101). The average power of the laser (101) at the samples on the substrate (102) is typically in the range 1 mW–1 W. The spacing of 12 ns is convenient for fluorescent lifetime detection, but can be varied as necessary, for example, by varying the cavity length of the laser (101). Common to both embodiments is the use of time-resolved imaging as a contrast-producing agent.

After leaving the laser (101), the excitation light (104) passes through one or more illumination optical elements to the substrate (102). The illumination optical elements can include an electro-optic modulator (108), a set of beam-shaping lenses (103), a scanning device (105), and a multi-element lens (109). The electro-optic modulator (108) can be used to modulate the polarization of the excitation light (104), if required by the investigation that is to be carried out on the samples on the substrate (102). The set of beam-shaping lenses (103) expands the laser beam in order to match the input aperture of the scanning lens and provide the desired illumination region size at the sample wells on the substrate (102). The scanning device (105) moves the expanded laser beam back and forth in a line-scan over the substrate (102) after the beam has been focused by the multi-element lens (109). The scanning device (105) can be an electromechanical device coupled to an optic element, such as a mirror driven by a galvanometer. In one embodiment, the scanning device (105) uses a polygon with multiple reflective surfaces to scan the laser beam across the substrate (102).

The multi-element lens (109) is designed to focus the laser light at the operating wavelength of the laser (101). The multi-element lens (109) can, for example, be a microscope objective designed for the operating wavelength or a specially designed scanning lens, such as a telecentric lens, that has appropriate parameters to achieve a flat focal plane, for example, with a long working distance and low first and second order aberrations, thus producing the same spot size and shape over a wide range of positions (such as a scan line). The telecentric lens is particularly useful for covering a large field of view. After passing the multi-element lens (109), the beam (110) is focused onto a region of the substrate (102) containing a sample to be imaged. The samples on the substrate (102) can be, for example, liquids, spots, beads, or cells that are to be interrogated by fluorescence.

The fluorescent light emitted by the samples is collected by one or more collection optical elements (119). There are several ways to configure the collection optical elements (119) that allow scanning of a large array of samples on a substrate. In one embodiment, the collection optical elements (119) is a rod lens, designed to capture the entire range of sweep of the beam (110) over one dimension of the substrate (102). The collection optical elements (119) can also include other types of lenses, or an aggregate of lenses, as would be determined by the specific information required from the emission. The collection optical elements (119) create a confined detection region, allowing an associated detector to only collect light from a relatively narrow area around the focal plane of the optical collection elements (119). In some embodiments, multiple setups of collection optical elements (119) can be used to improve collection efficiency, by further limiting the confined detection region to the intersection of the focal planes for each of the optical collection elements (119).

The light collected by the collection optical elements (119) is transmitted to a detector (121) located at a convenient distance from the collection optical elements (119). The transmission of the fluorescent light can be accomplished by, for example, an optical fiber or a bundle of optical fibers (120). In one embodiment, the detector (121) is a detector with high gain, such as a photomultiplier tube, which produces an electrical output signal. Specifically, the embodiment shown in FIG. 1 has two detectors (121), which each collect light of a particular polarization, selected by each set of optical elements (119). In the shown embodiment, each detector (121) has two different channels for polarization, which allows two-channel anisotropy measurements to be performed on the sample, and enables the use of internal anisotropy standards within the sample, which will be described in further detail below. The electrical output signal is further processed by a data acquisition system (114), connected to a computer (124) which performs operations such as optimization of the gain and the signal to noise ratio (S/N), by making use of signal enhancing, averaging, or integrating detection systems.

The system is typically implemented to include digital electronic circuitry, or computer hardware, firmware, software, or combinations of them, for example, in the controller (115), data acquisition system (114) and computer (124). Such features are commonly employed to control use of the substrates (both to deliver samples and interrogate samples disposed in the wells of the substrate). A system of the invention can be implemented to include a computer program product tangibly embodied in a machine-readable storage device for execution by a programmable processor; and method steps of the invention can be performed by a programmable processor executing a program of instructions to perform functions of the invention by operating on input data and generating output. The processor optionally can be coupled to a computer or telecommunications network, for example, an Internet network, or an intranet network, using a network connection, through which the processor can receive information from the network, or might output information to the network in the course of performing the method steps. Next, a process for detecting analytes in a target sample in accordance with one embodiment of the invention will be described with reference to FIG. 2.

Figure 2:
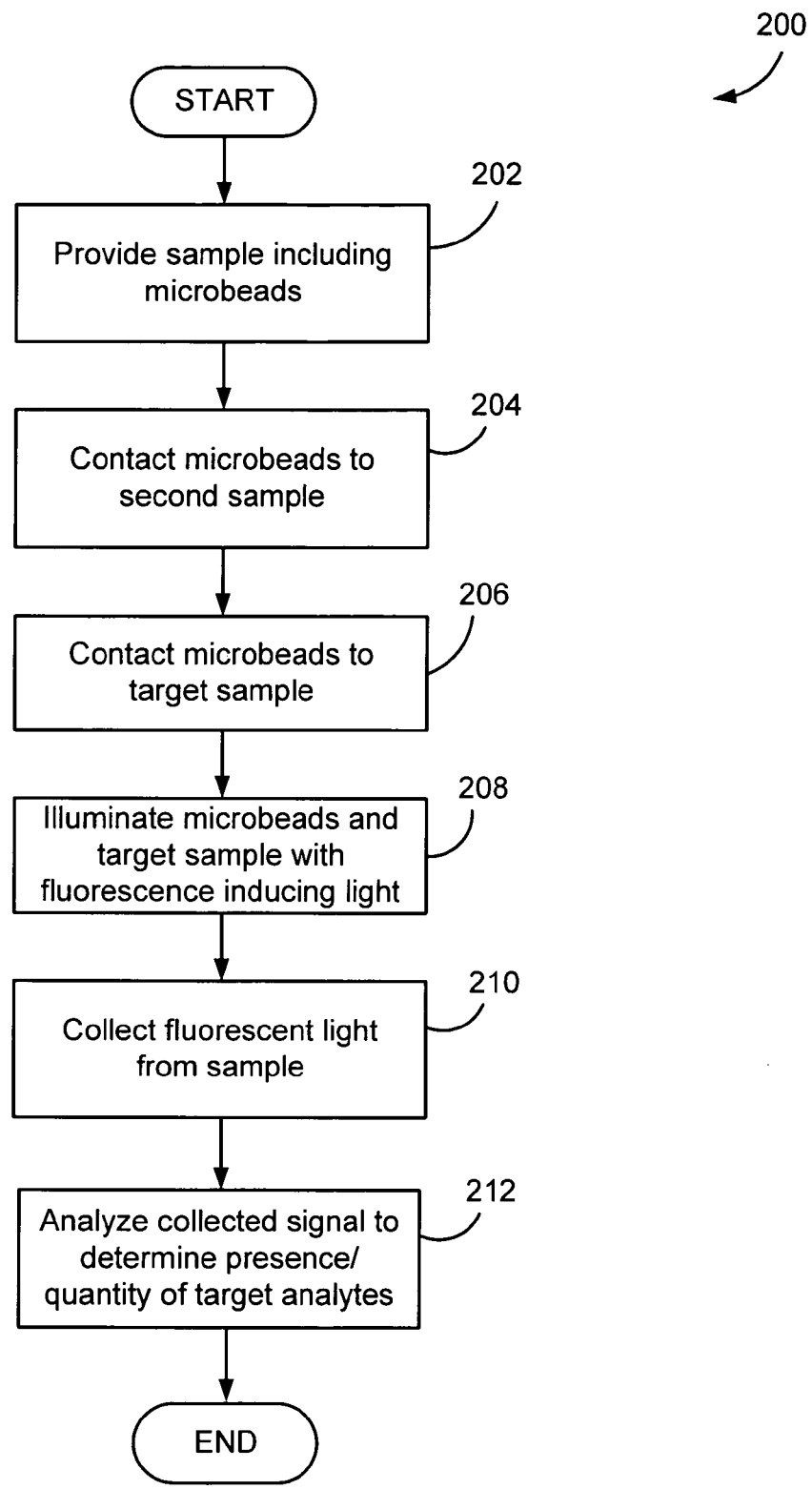
FIG. 2 shows a process for detecting analytes in a target sample in accordance with one embodiment of the invention.

As shown in FIG. 2, in one embodiment, a process (200) for detecting analytes in a target sample begins with providing a first sample that includes several optically encoded microbeads, which each has a specific affinity to a particular analyte (step 202). In this embodiment, the optically encoded microbeads are typically of about 0.1 to 20 microns in size, more typically about 1 to 10 microns in size, but in other applications the microbeads can have a size greater than about 20 microns. The predetermined, measurable and different optically encoded microbead characteristic can be of a unique size and/or have a unique response to light. The microbeads each have an optical signature corresponding to a particular analyte and can be optically encoded using single fluorophores or various ratios of fluorophore combinations, quantum dots, or other materials that have a response to light, such as phosphorescent materials. It should be noted that microbeads can also be encoded by other characteristics such as size, shape, location, or other methods known to those skilled in the art. This optical encoding works as a "barcode" for each of the microbeads and resides with the beads at all times, regardless of whether the beads are coupled to analytes or a label dependent on binding of analytes. It should also be noted that the optical encoding of the microbeads is not necessary to practice the invention, although some mechanism for distinguishing one sample from another is typically employed when multiple target analytes are to be detected. An example of location encoding is putting down an array of protein spots, where it is known that a certain spot contains a certain protein. For example, 4×4 arrays of protein spots can be employed, where each of the four members of the matrix is a different protein, having a pre-determined known spatial relationship to its peers.

The microbeads in the first sample are then contacted to a second sample that has at least one affinity moiety of a predetermined and specific affinity to a target analyte, or that has several predetermined and specific affinities to several target analytes (step 204). This causes the affinity moiety of the second sample to be bound to the microbeads of the first sample. The specific affinity moiety can be adsorbed onto the surface of the optically encoded microbeads, or can be covalently or non-covalently linked to the optically encoded microbeads. The specific affinity of each optically encoded microbead and the specific affinity of each affinity moiety can be, for example, an antibody, an antigen, a receptor, a ligand, a nucleic acid, an enzyme, a substrate and an inhibitor, or analogous moiety. As the skilled reader realizes, these affinity moieties are merely examples, and other affinity moieties are also possible.

The microbeads and their bound affinity moiety are then contacted to a target sample with several target analytes under conditions where the target analytes can bind to the affinity moiety (step 206). It should be noted that in the described embodiment, the contacting to the target analyte sample can take place under homogeneous assay conditions, that is, the assays do not involve any or minimal wash steps, which is typically necessary in order to remove unbound analytes in conventional assays, to prevent the unbound analytes from interfering with the bound analyte fluorescence measurements. Thus, the method and system in accordance with the invention offers a simpler and more rapid experimental procedure due to the lack of or reduction in the number of washing steps. The target analytes are typically dissolved or suspended in a solution. The target analytes can be, for example, antibodies, antigens, receptors, ligands, proteins, peptides, enzymes, nucleic acids, drugs, hormones, chemicals, pathogens, toxins, and combination thereof. Alternatively, the target analytes can be, for example, bacteria, viruses and combination thereof. It should, however, be noted that these target analytes are merely examples, and that other target analytes are also possible. Further, heterogeneous assays involving subsequent washing, and so on are not excluded in the practice of this invention.

Thereafter, the microbeads, along with the bound affinity moiety and any target analyte bound to the affinity moiety, are illuminated to induce fluorescence (step 208), and the fluorescent light is collected using the above-described analysis system (step 210). The above-described system allows several optical signals for each optically encoded microbead x-y location to be detected either simultaneously or sequentially. The fluorescence information is collected from a confined detection region, which allows for a homogenous assay format and provides high speed scanning. In one embodiment, the detection system can scan and analyze each optically encoded microbead in a planar array at a rate of up to 20,000 microbeads per second, or greater, classifying each optically encoded microbead based on its emitted optical signals, which include a fluorescent color and/or size signature. In another embodiment, the detection system can be used to scan and analyze each optically encoded microbead in a planar array at a rate of up to 20,000 beads per second, or greater, and detect several optical signals that are used to determine a presence of a particular analyte of the analytes in the target sample. The system can also be used to scan a defined area of the two-dimensional platform, for example, to read a barcode identifying the sample.

Based on the collected fluorescent signal the absence, presence and/or quantity of the target analytes in the target sample is determined (step 212), which ends the process. The determination for each optically encoded microbead results in several optical signals having, for example, a fluorescence intensity value, a fluorescence polarization/anisotropy state value, a rotational correlation time, and/or fluorescence lifetime values. The fluorescence intensity value can be used to determine the presence and/or amount of a particular analyte of the target analytes in the sample. The fluorescence polarization/anisotropy state value and/or rotational correlation time can be used to classify the microenvironment of a particular target analyte as well as the presence and/or amount. The classification of the microenvironment can be, for example, with respect to a local viscosity, whether the target analyte(s) are bound or unbound, whether there is a change in lifetime, a quenching event, a FRET (Foerster Resonanant Energy Transfer) event, and so on. Also, the fluorescence lifetime value can be used to classify the microenvironment of a particular analyte among target analytes in the sample. For example, in the case where FRET occurs between two moieties, the lifetime of the donor moiety will decrease. Determining the fluorescence lifetime signal provides a convenient method for making measurements of the molecular binding, since the unbound analytes do not interfere with the FRET measurements. FRET includes at least two different fluorophores bound to a respective one type of a target biomolecule or at least two different types of second biomolecules. Assays can be constructed using fluorophores including a fluorescent donor and a fluorescent acceptor that are optimally paired for FRET measurements. The fluorescent donor is typically a donor molecule having an emission spectrum. The fluorescent acceptor is an acceptor molecule having an absorption spectrum substantially in the same wavelength region as the donor spectrum. Energy is transferred between optimally paired fluorophores that are at a distance of 1 to 5 nanometers from each other.

The system also allows changes in the above signals with respect to time to be measured in order to provide kinetic information on the target and sample analytes. In many cases, kinetic rates are a superior method for quantitation of the amount or concentration of a particular analyte in a sample. The system can use several laser excitation and fluorescence emission wavelengths to enhance the method capabilities.

As the skilled reader realizes, the process of FIG. 2 can be varied in many ways. For example, in one embodiment, the microbeads that are not optically encoded and their corresponding analytes can be contained in discrete volume elements of the scanned sample, which makes it possible to gather information about the analytes based on the discrete volume elements of the target sample in which the analytes and microbeads are contained. The spatially differentiated fluorescence information can be used to determine a presence of a particular target analyte in a particular region. The spatially differentiated fluorescence information can include fluorescent light of a particular color from each target analyte.

In another embodiment, the optically encoded microbeads can be randomly distributed over predetermined spatial x-y locations (typically sample wells) on two-dimensional platforms or substrates, such as solid substrate surfaces, multi-well plates, or other sample containers. In yet another embodiment, the microbeads and the bound affinity moiety are repeatedly contacted to the target sample with analytes under conditions for the target analytes to bind to the affinity moiety several times, each time on a different x-y location of a two-dimensional platform or substrate.

Figure 3:
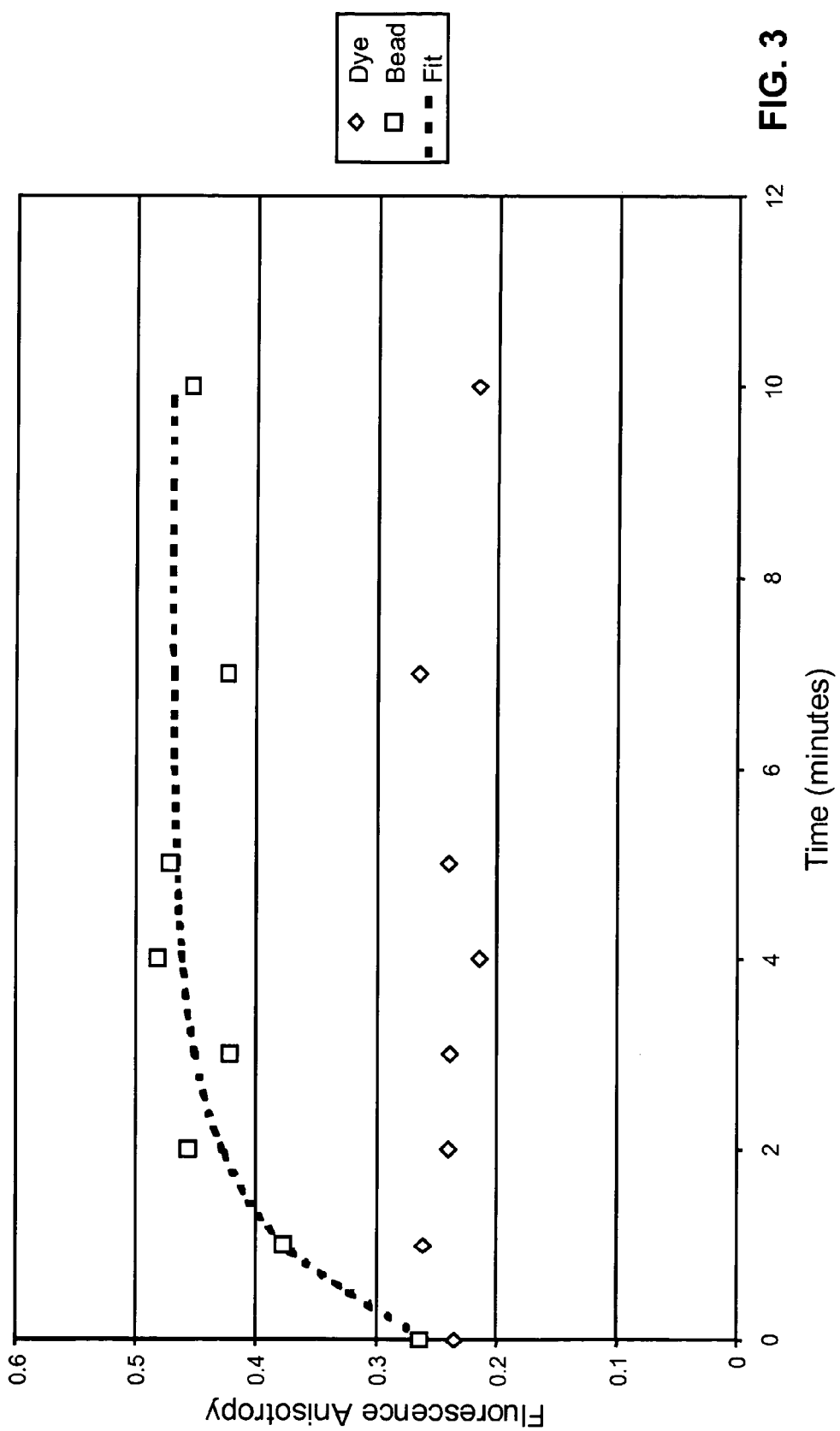
FIG. 3 shows a graph depicting the fluorescence anisotropy as a function of time for free fluorescent dye, and fluorescent dye that has been bound to microbeads, as registered by the system of FIG. 1, as well as a kinetic fit to the microbead fluorescence anisotropy.
Figure 4:
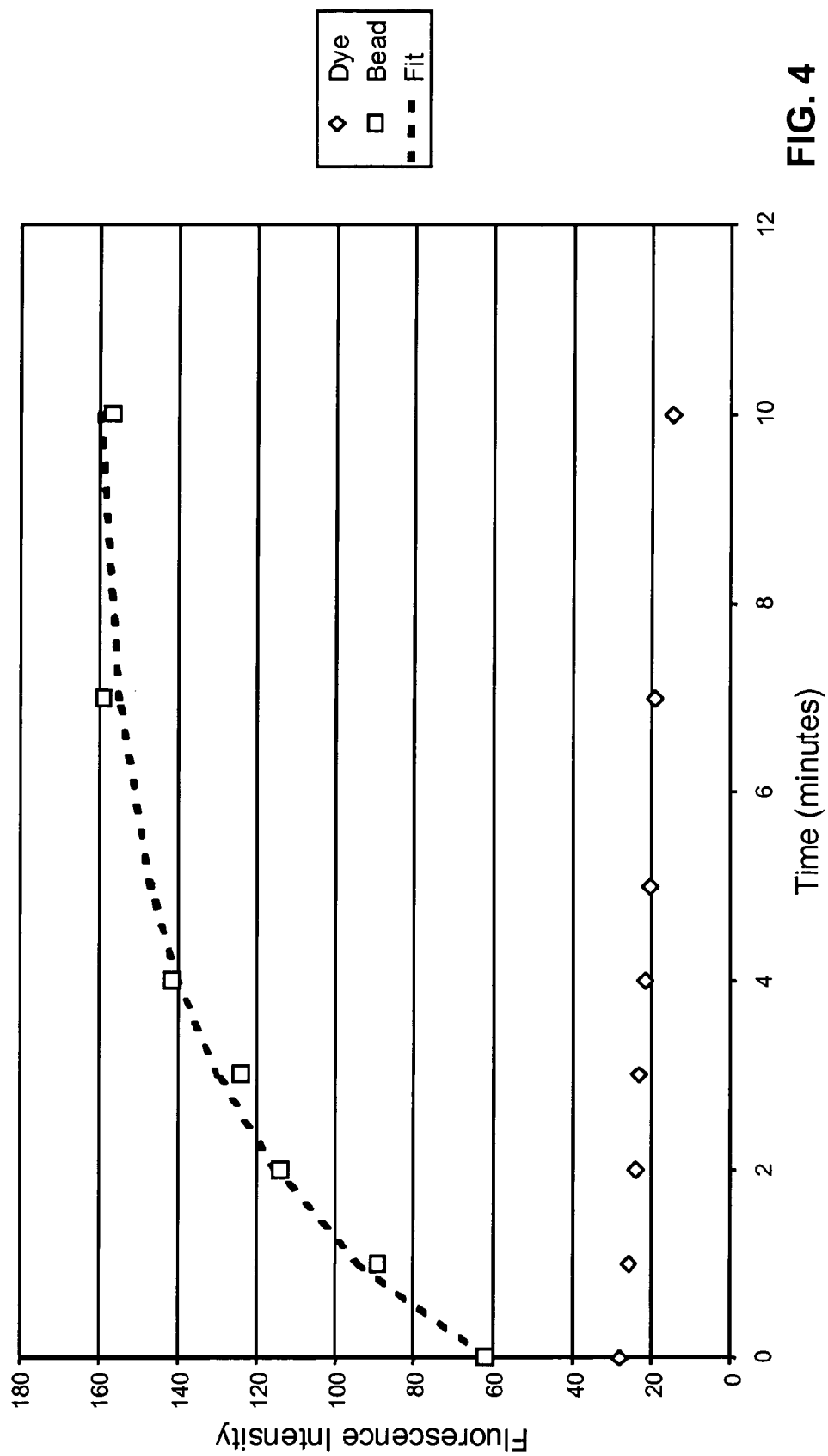
FIG. 4 shows a graph depicting the fluorescence intensity as a function of time for free fluorescent dye, and fluorescent dye that has been bound to microbeads, as registered by the system of FIG. 1, as well as a kinetic fit to the microbead fluorescence intensity.

FIG. 3 and FIG. 4 show some experimental results obtained in accordance with the above-described system and process. In the experiment illustrated in FIG. 3, 20 micron streptavidin-coated beads were combined with a 40 nM solution of conjugated Biotin-Alexa Fluor 564 Dye, and the anisotropy was measured. FIG. 3 shows a graph of the measured fluorescence anisotropy as a function of time, for a fluorescent dye in a solution (the diamond shaped data points in the lower part of FIG. 3) and fluorescent dye that is bound to microbeads (the square data points in the upper part of FIG. 3). Each data point in FIG. 3 corresponds to an average value measured over three microbeads. As can be seen in FIG. 3, the anisotropy is clearly higher for analyte that is bound to microbeads. Thus, the anisotropy value can be used to distinguish a microbead or other object in a solution from free fluorophores in the solution. As can also be seen in FIG. 3, the average anisotropy also increases during the early binding. The slope of the curve during the early binding stages can be used to quantify the initial concentration of target analyte present in the sample.

FIG. 4 shows the fluorescence intensity as a function of time for a fluorescent dye in a solution (the diamond shaped data points in the lower part of FIG. 4) and fluorescent dye that is bound to microbeads (the square data points in the upper part of FIG. 4) measured with the same system that was used to obtain the data illustrated in FIG. 3. As can be seen in FIG. 4, the fluorescent intensity for the dye bound to the beads or objects increases as a function of time until the microbeads or objects is saturated by the analyte. Also here, the slope of the early stages of this curve can be used to quantify the concentration of the analyte in the sample. The combination of anisotropy and fluorescence intensity can be used to enable homogeneous, or non-wash assays. As can be seen by comparing the graphs of FIG. 3 and FIG. 4, the anisotropy saturates much earlier than fluorescence intensity. Thus, the anisotropy can be used to define a region of interest, such as a microbead, spot, cell, or other object, where fluorescence intensity signals are subsequently measured. Any fluorescence originating outside the regions of interest can either be disregarded or be used as a background or other reference signal. That is, the anisotropy measurements are used as a gating or classification parameter for identifying the regions of interest on the sample where fluorescence intensity measurements should be made. In one embodiment, the anisotropy and intensity measurements can be performed by scanning whole sample using the above described system, and calculating an anisotropy value for every pixel in the scanned image of the sample, followed by a thresholding operation, such that intensity values are subsequently measured only for the sample regions of interest, that is, regions of the sample that have high anisotropy values.

In another embodiment, the ability of the analysis system to simultaneously detect anisotropy for two different colors is used to improve the anisotropy measurements. In this embodiment, a microbead (or other object) emits a fluorescence signal with a known anisotropy of a first wavelength or color. The target analyte emits a different fluorescence signal with an unknown anisotropy, as discussed above. By using the known anisotropy as an internal reference for the unknown anisotropy for the target analyte signal, an improved anisotropy value can be obtained for the target analyte signal. This technique avoids the problem of having to know the "g factor" in the anisotropy formula presented above, that is, the instrument and environment specific properties, and thus makes the anisotropy measurement more reliable.

Determination of analyte concentration from kinetic rates can be further understood as follows. Until the microbead is saturated with analyte species, the fluorescence intensity increases with the amount of analytes that bind to the microbeads until the microbeads are saturated. This can be seen in the bead curve of FIG. 4, which displays an increasing intensity during the early time intervals, which subsequently levels out to an almost horizontal curve after some time has passed. If the concentration of the analytes is low, then the required time to reach the saturation point will be longer, that is, the fluorescence intensity curve will have a lower slope. If the concentration of the analytes is high, then the required time to reach the end point will be shorter, that is, the slope of the fluorescence intensity curve will be steeper. Thus, by studying the slope of the fluorescence intensity curve for the beads as a function of time, and comparing the measured values to known analyte concentrations, information about the concentration of analytes in the sample can be derived. As the skilled reader realizes, the details of this method of determining analyte concentrations will depend on the order of the binding reaction and the relative binding rates (forward and reverse).

A number of implementations of the invention have been described. Nevertheless, it will be understood that various modifications may be made without departing from the spirit and scope of the invention. For example, the analysis method and system have been described above by way of example of an embodiment that uses the detection system of the above-referenced patent applications in conjunction with optically encoded microbeads, but any type of suitable objects or combinations of objects for moiety affinity can be used. Such examples of objects or combinations thereof include beads, spots, spot on spot, spot on a slide combined with a bead, cells, capillary tubes, microfluidic channels, and so on. An aspect of the invention common to many embodiments is the use an object that allows confinement of a sample to a well-defined region, a binding of analytes to the sample in the region, thereby allowing for detection of the presence, absence and/or quantity of the analytes in the target region. The methods and system have been described with respect to homogenous assays, but as the skilled reader realizes they can be equally applicable to heterogeneous assays as well as flow-based assays including lateral flow, capillary flow, and MEMS systems. Accordingly, other embodiments are within the scope of the following claims.

The invention claimed is:

1. A method for detecting a presence of one or more target analytes in particular regions of interest of one or more samples, the method comprising:
   providing one or more samples including a plurality of objects and one or more target analytes, wherein at least some of the target analytes are labeled with a fluorophore and are bound to at least some of the objects in the one or more samples;
   illuminating the one or more samples with fluorescence inducing light;
   collecting fluorescent light from one or more regions of the one or more samples;
   performing at least one anisotropy measurement of the one or more samples to identify one or more regions of interest where one or more target analytes are bound to the objects, wherein the regions of interest are identified as regions of the sample having a measured anisotropy value that exceeds a predetermined threshold value; and
   analyzing the collected fluorescent light from the regions of interest to determine a presence of target analytes that are bound to the objects in the one or more samples.

2. The method of claim 1, wherein:
   collecting fluorescent light includes collecting fluorescent light only from confined detection regions within the identified regions of interest.

3. The method of claim 1, wherein:
   analyzing the fluorescent light includes only analyzing fluorescent light collected from the identified regions of interest.

4. The method of claim 1, wherein the objects are selected from the group consisting of: spots, microbeads, cells, and microarrays.

5. The method of claim 1, wherein at least some of the plurality of objects are optically encoded by one or more of: fluorophores, quantum dots or other materials with a distinct response to excitation light.

6. The method of claim 1, wherein providing a sample includes:
   providing a plurality of optically encoded objects, each optically encoded object having an affinity to an analyte and having an optical signature corresponding to the analyte;
   contacting the objects with a sample containing one or more analytes having a first affinity moiety to at least one target analyte and a second affinity moiety to at least some of the optically encoded objects in the plurality of optically encoded objects, whereby the first affinity moiety of at least some analytes in the sample bind to the optically encoded objects; and
   contacting the optically encoded objects and their bound analytes with a target sample containing one or more target analytes under conditions allowing the target analytes to bind to the second affinity moiety of the analytes in the sample.

7. The method of claim 1, wherein analyzing includes one or more of: detecting a binding reaction occurring at one or more of the objects, classifying target analytes at one or more of the objects, and enumerating the one or more objects.

8. The method of claim 1, wherein the providing is performed under homogenous conditions that do not involve any wash steps.

9. The method of claim 6, wherein the second affinity moiety is selected from the group consisting of: an antibody, an antigen, a receptor, a ligand, a nucleic acid, an enzyme, a substrate inhibitor, and an analogous moiety.

10. The method of claim 1, wherein the target analytes include one or more of: an antibody, an antigen, a receptors, a ligand, a protein, a peptide, an enzyme, a nucleic acid, a drug, a hormone, a chemical, a pathogen, a toxin, a bacterium, or a virus.

11. The method of claim 1, wherein the collecting and analyzing steps are performed for up to about 20,000 objects per second.

12. The method of claim 5, wherein each optically encoded object is individually classifiable based on its emitted fluorescent light.

13. The method of claim 1, wherein the collecting step includes collecting one or more of: fluorescence intensity values, fluorescence polarization values, fluorescence anisotropy values, rotational correlation times, and fluorescence lifetimes.

14. The method of claim 1, wherein the illuminating, collecting and analyzing steps are performed in multiple fluorescence wavelength regions.

15. The method of claim 1, wherein analyzing further comprises measuring changes with respect to time of the collected fluorescent light to provide kinetic information.

16. The method of claim 15, further including determining concentrations for the one or more target analytes based on measured changes in intensity values of the collected fluorescent light over time.

17. The method of claim 15, further including determining concentrations for the one or more target analytes based on measured changes in anisotropy values of the collected fluorescent light over time.

18. The method of claim 15, further including determining individual objects in the plurality of objects that contain bound target analytes based on measured changes in anisotropy values of the collected fluorescent light over time.

19. The method of claim 1, further comprising:
providing a plurality of objects, each object having a known anisotropy, whereby an internal anisotropy reference is formed; and
wherein performing at least one anisotropy measurement includes comparing the measured anisotropy to the anisotropy of the objects with known anisotropy in order to obtain an improved anisotropy measurement of the bound target analyte.

* * * * *